(12) United States Patent
Rea et al.

(10) Patent No.: US 8,799,018 B1
(45) Date of Patent: Aug. 5, 2014

(54) PHARMACEUTICAL SYSTEMS AND METHODS

(71) Applicant: Rx Savings, LLC, Overland Park, KS (US)

(72) Inventors: Michael Rea, Overland Park, KS (US); Douglas Besch, Overland Park, KS (US)

(73) Assignee: RX Savings, LLC, Overland Park, KS (US)

( * ) Notice: Subject to any disclaimer, the term of this patent is extended or adjusted under 35 U.S.C. 154(b) by 0 days.

(21) Appl. No.: 14/071,247

(22) Filed: Nov. 4, 2013

Related U.S. Application Data

(60) Provisional application No. 61/722,525, filed on Nov. 5, 2012.

(51) Int. Cl.
| | |
|---|---|
| G06Q 50/00 | (2012.01) |
| G06Q 30/06 | (2012.01) |
| G06F 19/00 | (2011.01) |

(52) U.S. Cl.
CPC .......... G06Q 30/0631 (2013.01); G06F 19/328 (2013.01); G06Q 50/01 (2013.01)
USPC .................................................. 705/2; 705/3

(58) Field of Classification Search
CPC ...... G06Q 50/22; G06Q 50/24; G06F 19/326; G06F 19/3475
See application file for complete search history.

(56) References Cited

U.S. PATENT DOCUMENTS

| | | | |
|---|---|---|---|
| 7,426,476 | B2 | 9/2008 | Munoz et al. |
| 8,126,743 | B1 * | 2/2012 | Wilk ................................ 705/4 |
| 8,352,283 | B2 | 1/2013 | Ard et al. |
| 8,442,847 | B1 * | 5/2013 | Shrivastava ....................... 705/4 |
| 2002/0002504 | A1 | 1/2002 | Engel et al. |
| 2003/0120516 | A1 * | 6/2003 | Perednia ............................ 705/3 |
| 2005/0065821 | A1 * | 3/2005 | Kalies, Jr. ......................... 705/2 |
| 2005/0261939 | A1 * | 11/2005 | Augspurger et al. ............. 705/2 |
| 2007/0250341 | A1 * | 10/2007 | Howe et al. ....................... 705/2 |
| 2009/0006141 | A1 | 1/2009 | Karr |
| 2009/0083064 | A1 * | 3/2009 | Mahinda ............................ 705/2 |
| 2009/0106313 | A1 * | 4/2009 | Boldyga .................... 707/104.1 |
| 2010/0287001 | A1 * | 11/2010 | Pearce et al. ...................... 705/2 |
| 2011/0082711 | A1 | 4/2011 | Poeze et al. |
| 2012/0253830 | A1 * | 10/2012 | John et al. ......................... 705/2 |
| 2012/0323608 | A1 | 12/2012 | Herzlinger |
| 2013/0046610 | A1 | 2/2013 | Abraham |
| 2013/0173286 | A1 * | 7/2013 | Abeles ............................... 705/2 |
| 2013/0179180 | A1 | 7/2013 | Patra |

OTHER PUBLICATIONS

Ramirez, Leslie. "Tricks for helping patients save money on prescriptions". http://www.kevinmd.com/blog/2010/12/tricks-helping-patients-save-money-prescriptions.html. Published on Dec. 8, 2013.*

* cited by examiner

*Primary Examiner* — Sind Phongsvirajati
*Assistant Examiner* — Jonathan K Ng
(74) *Attorney, Agent, or Firm* — Lathrop & Gage LLP

(57) ABSTRACT

A system for determining a second drug and a third drug that may collectively be taken by a patient in lieu of a first drug prescribed to the patient by a physician comprises a processor in data communication with a non-transitory memory, an input device, an output device, and a networking device. The system also comprises a patients' database for storing a profile of the patient, and a drug pricing database for storing the first price, the second price, and the third price for the first, the second, and the third drugs, respectively. The first price is greater than a sum of the second and the third price. The system further comprises a drug segregation database for outlining that the first drug is segregable into the second drug and the third drug.

10 Claims, 22 Drawing Sheets

PROFILE 216A FOR CONSUMER
218A 220      222                    224                         226
Name of consumer    DOB         Contact Info                Currently taking medications
John Doe    01/01/1980          Phone: 123-456-7891         None.
                                Address: 123 Street, KS 66214
                                E-mail: JDoe@abc.com 228                       230                    232                   234
Medications previously taken    Allergies        Insurer               Physician
Drug B, 20 mg, 1/day      1. Substance YZ        Green Cross           Dr. Jane A (family physician)
                          2. Drug C              No.: 12345-6789

235                       236                    238
Pharmacy                  Prior reports 240R     Discount card 242C?
ABC Pharmacy-122 St., KS 66214    N/A            Yes

FIG. 3

| Column → | A | B | C | D | E | F | G |
|---|---|---|---|---|---|---|---|
| Row ↓ | | | DRUG PRICING DATABASE 206 | | | | |
| | | | Pharmacy Network 243A-Green Cross | | | | |
| 1 | ZIP 66214 | | | | | | |
| 2 | | Pharmacy | | | | | |
| 3 | | ABC | | | | | |
| 4 | | | Drug | Strength | Package Size | Cost per package | TM? |
| 5 | | | A® | (100/50) mg | 10 tablets | $20 | Y |
| 6 | | | | (100/50) mg | 20 tablets | $30 | |
| 7 | | | | (200/100) mg | 20 tablets | $40 | |
| 8 | | | | | | | |
| 9 | | | B | 20mg | 10 tablets | $5 | N |
| 10 | | | | 40mg | 10 tablets | $8 | |
| 11 | | | | | | | |
| 12 | | | C | 9 g | 1 tube | $100 | N |
| 13 | | | | | | | |
| 14 | | | D | 100mg | 10 tablets | $3 | N |
| 15 | | | | | | | |
| 16 | | | E | 50mg | 10 tablets | $4 | N |
| 17 | | | | | | | |
| 18 | | | F | (150/50) mg | 10 tablets | $25 | N |
| 19 | | | | | | | |
| 20 | | | G | (100/50) mg | 10 tablets | $15 | N |
| 21 | | | | | | | |
| 22 | | XYZ | | | | | |
| 23 | | | Drug | Strength | Package Size | Cost per package | |
| 24 | | | A® | (100/50) mg | 10 tablets | $25 | Y |
| 25 | | | | (100/50) mg | 20 tablets | $35 | |
| 26 | | | | (200/100) mg | 20 tablets | $45 | |
| 27 | | | | | | | |
| 28 | | | B | 20mg | 10 tablets | $5 | N |
| 29 | | | | 40mg | 10 tablets | $8 | |
| 30 | | | | | | | |
| 31 | | | C | N/A | | | N |
| 32 | | | | | | | |
| 33 | | | D | 100mg | 10 tablets | $4 | N |
| 34 | | | | | | | |
| 35 | | | E | 50mg | 10 tablets | $5 | N |
| 36 | | | | | | | |
| 37 | | | F | (150/50) mg | 10 tablets | $30 | N |
| 38 | | | | | | | |
| 39 | | | G | (100/50) mg | 10 tablets | $20 | N |
| 40 | | | | | | | |
| 41 | | WXY | | | | | |
| 42 | | | ..... | | | | |
| 43 | ZIP 66218 | ..... | | | | | |

FIG. 4A

| Column → | A | B | C | D | E | F | G |
|---|---|---|---|---|---|---|---|
| Row ↓ | | | DRUG PRICING DATABASE 206 | | | | |
| | | | Pharmacy Network 243B-Purple Cross | | | | |
| 1 | ZIP 66214 | | | | | | |
| 2 | | Pharmacy | | | | | |
| 3 | | ABC | | | | | |
| 4 | | | Drug | Strength | Package Size | Cost per package | TM? |
| 5 | | | A® | (100/50) mg | 10 tablets | $25 | Y |
| 6 | | | | (100/50) mg | 20 tablets | $35 | |
| 7 | | | | (200/100) mg | 20 tablets | $45 | |
| 8 | | | | | | | |
| 9 | | | B | 20mg | 10 tablets | $10 | N |
| 10 | | | | 40mg | 10 tablets | $18 | |
| 11 | | | | | | | |
| 12 | | | C | 9 g | 1 tube | $100 | N |
| 13 | | | | | | | |
| 14 | | | D | 100mg | 10 tablets | $5 | N |
| 15 | | | | | | | |
| 16 | | | E | 50mg | 10 tablets | $8 | N |
| 17 | | | | | | | |
| 18 | | | F | (150/50) mg | 10 tablets | $30 | N |
| 19 | | | | | | | |
| 20 | | | G | (100/50) mg | 10 tablets | $22 | N |
| 21 | | | | | | | |
| 22 | | XYZ | | | | | |
| 23 | | | Drug | Strength | Package Size | Cost per package | |
| 24 | | | A® | (100/50) mg | 10 tablets | $26 | Y |
| 25 | | | | (100/50) mg | 20 tablets | $36 | |
| 26 | | | | (200/100) mg | 20 tablets | $46 | |
| 27 | | | | | | | |
| 28 | | | B | 20mg | 10 tablets | $7 | N |
| 29 | | | | 40mg | 10 tablets | $9 | |
| 30 | | | | | | | |
| 31 | | | C | N/A | | | N |
| 32 | | | | | | | |
| 33 | | | D | 100mg | 10 tablets | $120 | N |
| 34 | | | | | | | |
| 35 | | | E | 50mg | 10 tablets | $8 | N |
| 36 | | | | | | | |
| 37 | | | F | (150/50) mg | 10 tablets | $33 | N |
| 38 | | | | | | | |
| 39 | | | G | (100/50) mg | 10 tablets | $22 | N |
| 40 | | | | | | | |
| 41 | | WXY | | | | | |
| 42 | | | ..... | | | | |
| 43 | ZIP 66218 | ..... | | | | | |

FIG. 4B

| DRUG SEGREGATION DATABASE 208 ||
|---|---|
| Drug (strength) | Constituent drug(s) (strength) |
| Drug A® (100/50 mg) | Drug D (100 mg) + Drug E (50 mg) |
| ….. ….. ….. | ….. ….. ….. |

FIG. 5

| THERAPEUTIC ALTERNATIVES DATABASE 210 ||
|---|---|
| Drug (strength) | Therapeutic Alternative(s) (strength) |
| A® (100/50 mg) | F (150/50 mg) |
| B (20 mg) | ……… |
| …… | ……… |
| …… | ……… |
| …… | ……… |

FIG. 6

| GENERICS DATABASE 212 ||
|---|---|
| Drug (strength) | Generic (strength) |
| A® (100/50 mg) | G (100/50 mg) |
| ...... ..... ..... ..... | ....... ....... ....... ....... |

FIG. 7

| DRUG INGREDIENTS DATABASE 213 | |
|---|---|
| DRUG | INGREDIENTS |
| A® | Substance FG, Substance FH, Substance FJ |
| B | Substance FK, Substance FL, titanium oxide |
| C | Substance GH, Substance GK, Substance KL |
| D | Substance FG, Substance FH |
| E | Substance FJ |
| F | Substance YZ, Substance FL |
| G | Substance FG, Substance FH, Substance FJ |
| ..... | ....... |
| ..... | ....... |
| ..... | ....... |
| ..... | ....... |

FIG. 8

| PROMOTIONAL OFFER DATABASE 214 ||
|---|---|
| DRUG | PROMOTIONAL OFFER |
| A® | 10% off coupon (250A), no expiration, at www.drugAmanufacturer.com |
| B | 50% off coupon (250B) at Pharmacy XYZ, no expiration, in Publication Q |
| ..... | ..... |

FIG. 9

TEMPORARY RECORD 280 OF THE CONSUMER 218A

Option 0 (original prescription): Drug A®, 270 tablets, (100/50) mg each

FIG. 11A

TEMPORARY RECORD 280 OF THE CONSUMER 218A

Option 0 (original prescription): Drug A®, 270 tablets, (100/50) mg each

Option 1 (generic substitute): Drug G, 270 tablets, (100/50) mg each

FIG. 11B

TEMPORARY RECORD 280 OF THE CONSUMER 218A

Option 0 (original prescription): Drug A®, 270 tablets, (100/50) mg each

Option 1 (generic substitute): Drug G, 270 tablets, (100/50) mg each

Option 2 (drug segregation): Drug D, 270 tablets, 100 mg each plus Drug E, 270 tablets, 50 mg each

FIG. 11C

TEMPORARY RECORD 280 OF THE CONSUMER 218A

Option 0 (original prescription):   Drug A®, 270 tablets, (100/50) mg each

Option 1 (generic substitute):   Drug G, 270 tablets, (100/50) mg each

Option 2 (drug segregation):   Drug D, 270 tablets, 100 mg each plus Drug E, 270 tablets, 50 mg each Option 3 (therapeutic equivalent):   Drug F, 270 tablets, (150/50) mg each

FIG. 11D

TEMPORARY RECORD 280 OF THE CONSUMER 218A

Option 0 (original prescription):   Drug A®, 270 tablets, (100/50) mg each

Option 1 (generic substitute):   Drug G, 270 tablets, (100/50) mg each

Option 2 (drug segregation):   Drug D, 270 tablets, 100 mg each plus Drug E, 270 tablets, 50 mg each Option 3 (therapeutic equivalent):   Drug F, 270 tablets, (150/50) mg each Option 4 (tablet splitting):   Drug A®, 135 tablets, (200/100) mg each

FIG. 11E

TEMPORARY RECORD 280 OF THE CONSUMER 218A

Option 0 (original prescription): Drug A®, 270 tablets, (100/50) mg each

Option 1 (generic substitute): Drug G, 270 tablets, (100/50) mg each

Option 2 (drug segregation): Drug D, 270 tablets, 100 mg each plus Drug E, 270 tablets, 50 mg each ~~Option 3 (therapeutic equivalent):   Drug F, 270 tablets, (150/50) mg each~~

Option 4 (tablet splitting): Drug A®, 135 tablets, (200/100) mg each

FIG. 11F

TEMPORARY RECORD 280 OF THE CONSUMER 218A

Option 0 (original prescription):     Drug A®, 270 tablets, (100/50) mg [10% off coupon 250A]

Option 1 (generic substitute):     Drug G, 270 tablets, (100/50) mg each

Option 2 (drug segregation):     Drug D, 270 tablets, 100 mg each plus Drug E, 270 tablets, 50 mg each ~~Option 3 (therapeutic equivalent):~~     ~~Drug F, 270 tablets, (150/50) mg each~~

Option 0 (original prescription):     Drug A®, 270 tablets, (200/100) mg [10% off coupon 250A]

FIG. 11G

| TEMPORARY RECORD 280 OF THE CONSUMER 218A | |
|---|---|
| Option 0 (original prescription): Drug A®, 270 tablets, 100/50 mg each [10% off coupon 250A] | $ 369 at Pharmacy ABC (zip 66214) |
| Option 1 (generic substitute): Drug G, 270 tablets, 100/50 mg each | $ 405 at Pharmacy ABC (zip 66214) |
| Option 2 (drug segregation): Drug D, 270 tablets, 100 mg plus Drug E, 270 tablets, 50 mg | $ 189 at Pharmacy ABC (zip 66214) |
| ~~Option 3 (therapeutic equivalent): Drug F, 270 tablets, 150/50 mg each~~ | |
| Option 4 (tablet splitting): Drug A®, 135 tablets, 200/100 mg each [10% off coupon 250A] | $252 at Pharmacy ABC (zip 66214) |
| Cost Effective Option 272 = Option 2 (drug segregation) | |

FIG. 11H

PHARMACEUTICAL SYSTEMS AND METHODS

CROSS-REFERENCE TO RELATED APPLICATIONS

This application claims priority to U.S. Provisional Patent Application Ser. No. 61/722,525 filed Nov. 5, 2012, the disclosure of which is incorporated herein by reference in its entirety.

FIELD OF THE INVENTION

The invention relates generally to the field of pharmaceuticals. More specifically, the invention relates to systems and methods for reducing costs incurred by patients and their health insurance carriers in fulfilling the patients' medicinal needs.

SUMMARY

Systems and methods for determining cost effective alternatives to drugs prescribed to patients are disclosed herein. According to an embodiment, a computer implemented method for determining a cost effective alternative to a first drug prescribed to a patient by a physician comprises the step of using a generics database to identify a second drug that is a generic alternative of the first drug. The method further comprises the steps of using a therapeutic alternatives database to identify a third drug that is a therapeutic alternative of the first drug, and using a drug segregation database to identify both a fourth drug and a fifth drug into which the first drug can be segregated. The second drug is stored in non-transitory computer memory as a first option. The third drug is stored in the non-transitory computer memory as a second option. The fourth and the fifth drugs are collectively stored in the non-transitory computer memory as a third option. A drug pricing database is used to determine an original price of the first drug, a first price of the first option, a second price of the second option, and a third price of the third option. The first price, the second price, and the third price are compared to identify a lowest price that is less than the original price, and the cost effective alternative is identified as the option that corresponds to the lowest price. A report is generated for the patient using an output device. The report has a first portion outlining the cost effective alternative and a second portion including a note for the physician.

According to another embodiment, a system for determining a cost effective alternative to a first drug prescribed to a patient by a physician comprises a processor in data communication with a non-transitory memory, an input device, an output device, and a networking device. The system further comprises a generics database for identifying a second drug that is a generic alternative of the first drug, and a therapeutic alternatives database for identifying a third drug that is a therapeutic alternative of the first drug. The system also includes a drug segregation database for identifying both a fourth drug and a fifth drug into which the first drug is segregable, and a drug ingredients database for identifying an ingredient of the third drug. The system further comprises a promotional offer database for identifying a promotional offer applicable to at least one of the first drug, the second drug, the third drug, the fourth drug, and the fifth drug, and a drug pricing database for identifying a first price of the first drug, a second price of the second drug, a third price of the third drug, a fourth price of the fourth drug, and a fifth price of the fifth drug. The second price of the second drug is the lower of a sixth price and a seventh price. The sixth price is the price of the second drug under a first pharmacy network, and the seventh price is the price of the second drug under a second pharmacy network.

According to yet another embodiment, a system for determining a second drug and a third drug that may collectively be taken by a patient in lieu of a first drug prescribed to the patient by a physician is disclosed. The first drug has a first price, the second drug has a second price, and the third drug has a third price. The system comprises a processor in data communication with a non-transitory memory, an input device, an output device, and a networking device, and a patients' database for storing a profile of the patient. The system further comprises a drug pricing database for storing the first price, the second price, and the third price, and a drug segregation database for outlining that the first drug is segregable into the second drug and the third drug. The first price is greater than a sum of the second price and the third price.

BRIEF DESCRIPTION OF THE SEVERAL VIEWS OF THE DRAWINGS

Illustrative embodiments of the present invention are described in detail below with reference to the attached drawing figures and wherein:

FIG. 3 shows an exemplary profile of a consumer as saved in a consumer database of the pharmaceutical databank of FIG. 2.

FIGS. 4A-4B show exemplary contents of a drug pricing database of the pharmaceutical databank of FIG. 2.

FIG. 5 shows exemplary contents of a drug segregation database of the pharmaceutical databank of FIG. 2.

FIG. 6 shows exemplary contents of a therapeutic alternatives database of the pharmaceutical databank of FIG. 2.

FIG. 7 shows exemplary contents of a generics database of the pharmaceutical databank of FIG. 2.

FIG. 8 shows exemplary contents of a drug ingredients database of the pharmaceutical databank of FIG. 2.

FIG. 9 shows exemplary contents of a promotional offer database of the pharmaceutical databank of FIG. 2.

FIGS. 11A through 11H illustrate a temporary record created by the system of FIG. 1 to effectuate performance of the method in FIGS. 10A through 10B.

DETAILED DESCRIPTION

The healthcare system in the United States, at least according to some estimates, is inefficient. For example, a recent survey by the Bloomberg Company indicates that the healthcare system in the United States is among the most inefficient healthcare systems in the world. It is no surprise then that healthcare costs in the United States have steadily increased for the past several years. The costs incurred by consumers (e.g., patients) in purchasing the pharmaceutical drugs they require have likewise soared. For many consumers, these costs of pharmaceutical drugs have now become prohibitive.

There is a dire need for a system that allows consumers to fulfill their medicinal needs at reduced out-of-pocket costs. Embodiments of the present invention provide systems and methods for addressing this problem. The systems and methods disclosed herein may also be used to reduce costs incurred by the health insurance carriers of consumers (e.g., commercial health insurance companies employed by the consumers and/or the consumers' employers, self-insured employers of the consumers, et cetera).

Figure 1:
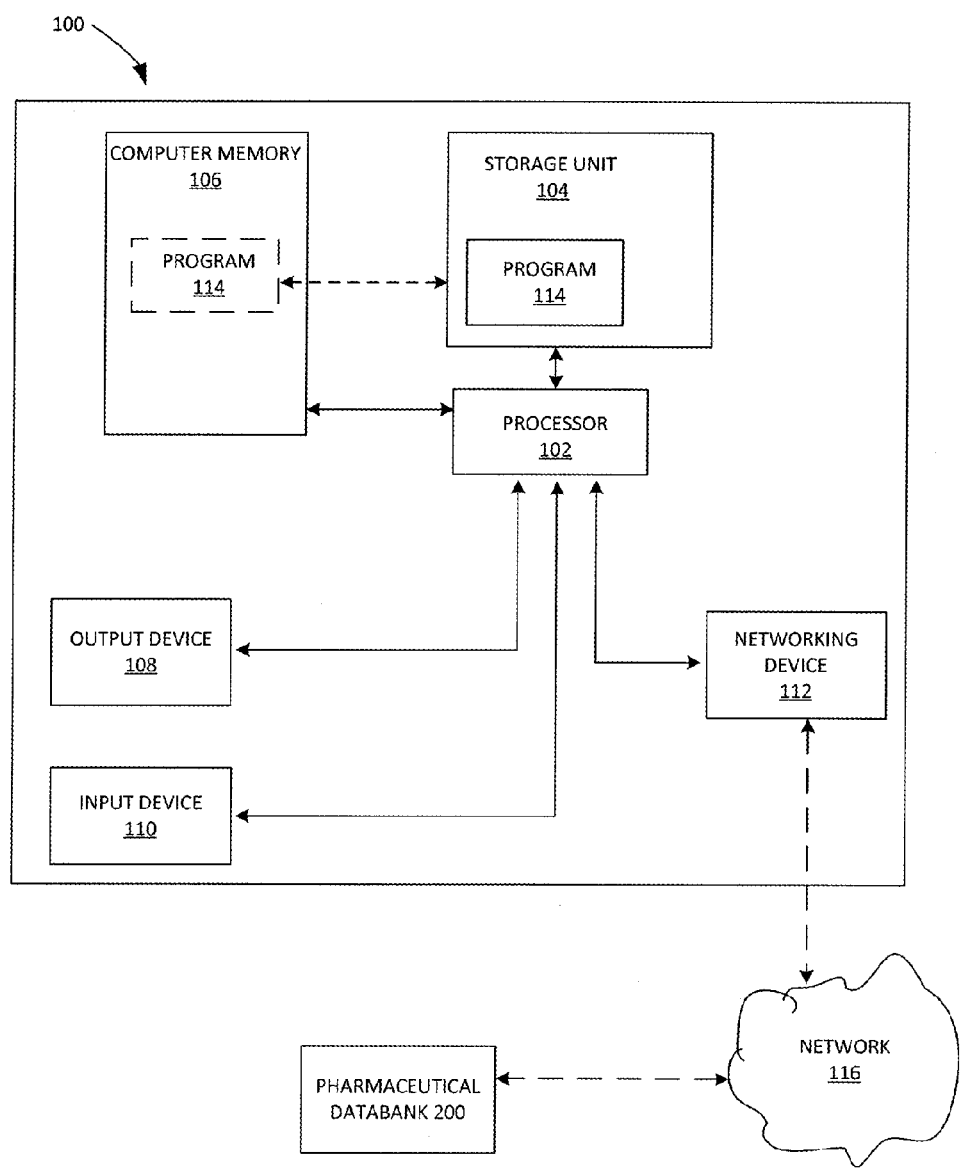
FIG. 1 shows a schematic illustrating electronic communication between various components of a pharmaceutical system, according to an embodiment of the present invention.

Attention is directed now to FIG. 1, which shows a pharmaceutical system 100 in line with the teachings of the current invention. The pharmaceutical system 100 may comprise a processor (or controller) 102 in data communication with a storage unit 104, a computer memory 106, an output device 108, an input device 110, and a networking device 112.

The storage unit 104 may be, for example, a disk drive that stores programs and data (i.e., non-transitory memory), and the storage unit 104 is illustratively shown storing a program 114 embodying the steps and methods set forth below. It should be understood that the program 114 could be broken into subprograms and stored in storage units of separate devices and that data could be transferred between those storage units using methods known in the art. A dashed outline within the computer memory 106 represents the software program 114 loaded into the computer memory 106 and a dashed line between the storage unit 104 and the computer memory 106 illustrates the transfer of the program 114 between the storage unit 104 and the computer memory 106.

The output device 108 may include one or more display monitors (e.g., CRT monitors, LCD or Plasma display devices, et cetera), speakers, printers, or any other appropriate video and/or audio output device whether now known or later invented. The input device 110 may comprise keys, switches, knobs, infrared or other sensors, remote controllers, microphones, stylus pens, touch screens, input slots (e.g., CD, DVD, USB, SD card input slots), barcode or other scanners, et cetera. The networking device 112 may be any networking device that allows the system 100 to communicate over a network 116, such as a switch, a wireless router, a wired modem, a networking card, a transmitter, a receiver, et cetera. The network 116 may be, for example, the World Wide Web, or a private or local network. The network 116 may be secured (e.g., password protected) and/or encrypted in line with any networking technologies that are now known or later invented. While not expressly shown, in some embodiments, the networking device 112 may additionally be configured to communicate over cellular networks.

The networking device 112 may allow the system 100 to communicate via the network 116 with a pharmaceutical databank 200. The communication between the system 100 and the pharmaceutical databank 200 may be effectuated wirelessly, which may allow many different systems 100 located in varying geographic locations to seamlessly access the databank 200. In some embodiments, however, the communications between the system 100 and the databank 200 may be effectuated using a wired connection. Further, in some embodiments, data in the databank 200 may additionally or alternatively be stored in the storage unit 104.

Figure 2:
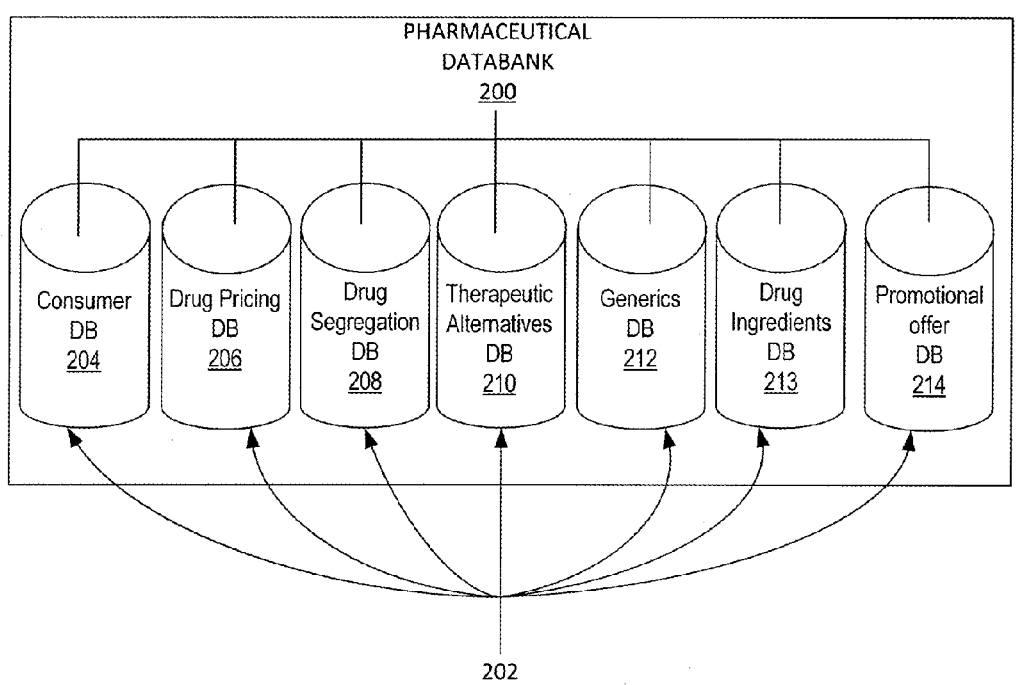
FIG. 2 shows constituent databases of a pharmaceutical databank in communication with the system of FIG. 1.

The pharmaceutical databank 200 may comprise a plurality of databases 202. For example, as shown in FIG. 2, the databank 200 may include a consumer (or patients' or users') database 204, a drug pricing database 206, a drug segregation database 208, a therapeutic alternatives database 210, a generics database 212, a drug ingredients database 213, and a promotional offer (or coupon) database 214.

The consumer (or patients') database 204 may include information about the consumers 218. In some embodiments, the consumer database 204 may include a plurality of consumer profiles 216, and each profile 216 may include multiple fields comprising information about a specific consumer (or patient) 218. For example, each consumer profile 216 may have a field 220 for outlining the name of the consumer 218; a field 222 for outlining the date of birth of the consumer 218; a field 224 for outlining the contact information (e.g., phone number, residential address, e-mail address, et cetera) of the consumer 218; a field 226 for outlining any medications that the consumer 218 is currently taking along with the quantity or strength of such medications and the frequency with which the consumer 218 is taking these medications; a field 228 for outlining any medications that the consumer 218 has taken in the past (e.g., in the last five years); a field 230 for outlining any substances or drugs to which the consumer 218 is allergic; a field 232 for outlining the insurer and insurance policy number of the consumer 218, if available; and a field 234 for outlining the one or more physicians that the consumer 218 visits; and a field 235 for identifying the pharmacy (e.g., by name and address) that the consumer 218 prefers to utilize when obtaining his medications. The profile 216 may further include a field 236 for outlining any prior reports 240R that have been generated on behalf of the consumer 218, and a field 238 for outlining whether the consumer 218 has obtained a discount card 242C, which reports 240R and discount card 242C are discussed in more detail herein.

In some embodiments, the data associated with the consumer 218 may be collected from the consumer 218 himself (e.g., by causing the consumer 218 to fill out a paper or online form) and compiled thereafter in the profile 216 using the system 100. In some embodiments, all or part of this data may be collected using one or more external sources. For example, data associated with the consumer 218 may be collected from the consumer's employer and/or health insurance carrier. Of course, when obtaining data about the consumer 218 from external sources (and also when obtaining the data about the consumer 218 from the consumer 218 himself), care may be taken to ensure that all applicable laws (e.g., medical privacy laws) are complied with as required. People of skill in the art will appreciate that the fields in the profile 216 are exemplary only; in some embodiments, one or more of the fields may be omitted from the profile 216, whereas in other embodiments, additional fields may be provided for including additional information about the consumer 218 in his profile 216. For example, in some embodiments, the profile 216 may include a field for outlining the social security (or other identification) number associated with the consumer 218. Similarly, in some embodiments, a field may be provided in the profile 216 for outlining the identification number of the employer of the consumer 218.

FIG. 3 illustrates an exemplary profile 216A for a consumer 218A named John Doe. As can be seen, John Doe's name (field 220), date of birth (field 222), contact information (field 224), current medications (field 226), past medications (field 228), allergies (field 230), insurer and policy number (field 232), physician(s) (field 234) and preferred pharmacy (field 235) are each outlined in his profile 216A. The profile 216A further indicates that no prior reports 240R have been generated for John Doe (field 236), and that John Doe possesses a discount card 242C (field 238). While FIG. 3 illustrates one profile 216A associated with a consumer 218A, people of skill in the art will appreciate that many (e.g., hundreds of thousands) such profiles 216 regarding many additional consumers 218 may likewise be saved in the consumer database 204 of the pharmaceutical databank 200.

It is common knowledge that prices of drugs may vary from one geographical area to another, and also between two different pharmacies within the same geographical area. Further, each pharmacy may be a part of multiple pharmacy networks (e.g., multiple pharmacy networks negotiated by multiple pharmacy benefit managers), and the price of the same drugs may vary within the same pharmacy based on the application of these different pharmacy networks. The drug pricing database 206 of the databank 200 may include a listing of prices of all (or all or most commonly available) drugs, organized by geographical area (e.g., by zip code) and pharmacy name available under each pharmacy network 243. FIGS. 4A-4B show spreadsheets illustrating exemplary contents of the drug pricing database 206. To facilitate discussion, reference will be made herein to certain discrete cells of the spreadsheets of FIGS. 4A-4B. These cells will be referenced by their column and row number. For example, cell F5 and cell F39 of FIG. 4A both list the value "$20."

As can be appreciated from FIG. 4A, the drug pricing database 206 may outline that the exemplary zip code 66214 (cell A1) includes three pharmacies (i.e., Pharmacy ABC (cell B3), Pharmacy XYZ (cell B22) and Pharmacy WXY (cell B41)). The drug pricing database 206 may further outline the various drugs carried by these pharmacies, along with the drugs' respective prices at these pharmacies under each (or many) pharmacy network 243. Assume for the purposes of illustration that the insurer Green Cross (field 232 in profile 216A) of the consumer 218A is associated with a first pharmacy network 243A. The drug pricing database 206 may outline that under the pharmacy network 243A: a package of ten 100/50 mg tablets (cells D5, E5) of drug A® (100/50 mg) (cell C5) are being sold at pharmacy ABC (cell B3) for $20 (cell F5); a package of twenty 100/50 mg tablets (cells D6, E6) of drug A® (100/50 mg) (cell C5) are being sold at Pharmacy ABC (cell B3) for $30 (cell F6); and a package of twenty 200/100 mg tablets (cells D7, E7) of drug A® (200/100 mg) (cell C5) are being sold at Pharmacy ABC (cell B3) for $40 (cell F7). Similarly, for example, the pricing database 206 may outline that under the pharmacy network 243A, a package of ten 100/50 mg tablets (cells D24, E24) of drug A® (100/50 mg) (cell C24) are being sold at pharmacy XYZ (cell B22) for $25 (cell F24); a package of twenty 100/50 mg tablets (cells D25, E25) of drug A® (100/50 mg) (cell C24) are being sold at Pharmacy XYZ (cell B22) for $30 (cell F25); and a package of twenty 200/100 mg tablets (cells D26, E26) of drug A® (200/100 mg) (cell C24) are being sold at Pharmacy XYZ (cell B22) for $45 (cell F26). Additionally, for example, as can be seen in FIG. 4A, the drug pricing database 206 may outline that a package comprising ten 100 mg tablets of drug D are being sold at Pharmacy ABC and Pharmacy XYZ for $3 and $4, respectively, under the pharmacy network 243A. The drug pricing database 206 may also set forth whether each drug listed therein is trademarked; for example, the drug pricing database 206 may outline that Drug A is a trademarked drug (cells G5, G24).

Similarly, as shown in FIG. 4B, the drug pricing database 206 may outline the prices of various drugs under a second pharmacy network 243B (which may be a discount network or a network associated with a different insurer (e.g., Purple Cross)). For example, as shown in FIG. 4B, the price of ten tablets of Drug A® (100/50 mg) at Pharmacy ABC in zip code 66214 may be $25 under the second pharmacy network 243B.

While the spreadsheets at FIGS. 4A-4B refer to only three pharmacies (i.e., a first Pharmacy ABC, a second Pharmacy XYZ and third Pharmacy WXY) within the zip code 66214 and outlines prices of various packages of only seven drugs (i.e., Drugs A® through G) under two pharmacy networks 243 (i.e., the first pharmacy network 243A and the second pharmacy network 243B), people of skill in the art will appreciate that the drug pricing database 206 may similarly include such information about every pharmacy within every geographical region (e.g., every zip code), including the prices of all drugs carried by each of these pharmacies under each of the various pharmacy networks 243. Information in the drug pricing database 206 (and the remaining databases 202 in the pharmaceutical databank 200) may be readily and remotely updated over the network 116 (e.g., via a web-based interface, not specifically shown). In some embodiments, data may be automatically pulled in from external sources for compilation in the drug pricing database 206. For example, the prices of drugs carried by Pharmacy ABC may be automatically updated in the drug pricing database 206 by linking the pricing database 206 with an inventory management or other system used by Pharmacy ABC. In some embodiments, the prices of drugs under each pharmacy network 243 may be obtained from the respective pharmacy benefit managers associated with that pharmacy network 243. In some embodiments, some or all of the information in the pricing database 206 (and the other databases 202) may be compiled and updated manually by authorized personnel (e.g., owners or operators of the system 100).

Attention is directed now to FIG. 5, which shows exemplary contents of the drug segregation database 208. People of skill in the art will appreciate from the disclosure herein that many drugs (or their active ingredients) are composed by combining two or more constituent drugs, and that often, the constituent drugs are also separately available for sale. For example, as shown in FIG. 5, each 100/50 mg tablet of drug A® (100/50 mg) may comprise 100 mg of drug D and 50 mg of drug E, and each of these drugs A, D, and E may be separately purchasable (see FIG. 4A). While the drug segregation database 208 shows only drug A® as being segregable, people of skill in the art will appreciate that the drug segregation database 208 may similarly include a listing of each (or many) drug so segregable, along with the constituent drugs comprising the segerable drug. Data in the drug segregation database 208 may be conveniently updated (e.g., remotely over the network 116) as new segregable drugs are introduced into (or removed from) the pharmaceutical market.

FIG. 6 shows exemplary contents of the therapeutic alternatives database 210. The therapeutic alternatives database 210 may outline, where applicable, the therapeutic alternative(s) of each drug. For example, as shown in FIG. 6, the therapeutic alternatives database 210 may outline that a 100/50 mg tablet of Drug A® (100/50) is therapeutically equivalent to a 150/50 mg tablet of Drug F. The term "therapeutic alternative" as used herein is not meant to encompass generic alternatives of drugs (discussed further below, which include the same active ingredients as the base drug). Rather, the term therapeutic alternative(s) is used herein to refer to those drugs which have different active ingredients but similar therapeutic affects as the base drug. People of skill in the art will thus appreciate that Drug A® and Drug F have disparate active ingredients, but that both these drugs may advantageously diminish the adverse effects of a particular ailment(s) in similar fashion. People of skill in the art will further appreciate that while FIG. 6 outlines a therapeutic alternative for only Drug A®, that one or more therapeutic alternatives may similarly be outlined for each drug that has a therapeutic equivalent.

Attention is directed now to FIG. 7, which shows exemplary contents of the generic database 212. People of skill in the art will appreciate that many trademarked drugs (e.g., drug A®) have a generic version(s) that: (a) includes the same active ingredients as the trademarked drug; and (b) is generally offered for sale at a cheaper price as compared to the trademarked drug. For example, the generics database 212 may outline that drug G (100/50 mg) (which is being offered for sale at each respective pharmacy at a cheaper price than Drug A® (see FIG. 4A at cells F5, F20, F24, and F40)) is the generic version of trademarked drug A (100/50 mg). Of course, in some instances, the trademarked drug may be purchased at a cheaper price as compared to the generic version (e.g., when the trademarked drug is discounted under a promotional offer (discussed further below)). While FIG. 7 shows the generic version of only drug A®, those skilled in the art will readily recognize that the generics database 212 may similarly set forth where applicable the generic version(s) of each trademarked drug currently offered for sale. As with the other database 202, data in the generics database 212 may be conveniently updated (e.g., remotely over the network 116) as additional trademarked drugs and/or generics are introduced into the market.

FIG. 8 shows exemplary contents of the drug ingredients database 213. The drug ingredients database 213 may set forth the ingredients of each drug currently available for purchase by the consumer 218A. For example, as shown in FIG. 8, the drug ingredients database 213 may outline that Drug A® and its generic version Drug G both comprise exemplary substances FG, FH, and FJ. Similarly, for example, the drug ingredients database 213 may set forth that a drug F comprises exemplary substances YZ and FL. The ingredients of other drugs may similarly be provided in the drug ingredients database 213.

FIG. 9 shows exemplary contents of the promotional offer database 214. From time to time, pharmaceutical drug manufacturers (or retailers) may offer (via newspaper(s), medical publication(s), coupons, website(s), et cetera) promotional offers 250 on certain drugs. These promotional offers 250 may extend to all drugs made by the drug manufacturer or be limited to a solitary drug, and may be applicable only in a particular geographical area or pharmacy. For example, as shown in FIG. 9, the manufacturer of the drug A® may disseminate a coupon 250A via its website that allows the consumer 218 to purchase the drug A® at a 10% price reduction. Similarly, Pharmacy XYZ may offer a coupon 250B in a medical publication Q that enables consumers to purchase the drug B at half price. Those skilled in the art will appreciate that several promotional offers 250, while available to the consumer 218, remain unutilized because the consumer 218 is unaware of the existence of the promotional offer 250. Several mechanisms may be employed in tandem to ensure that each (or many) available promotional offers 250 are compiled in the promotional offer database 214 and are utilized as set forth herein where desirable. For example, the program 114 may include programming that scours the World Wide Web to search for and compile in the promotional offer database 214 any promotional offers 250 posted on the World Wide Web. Additionally, for example, authorized personnel may monitor print media to ensure that any promotional offers 250 regarding pharmaceutical drugs are adequately referenced in the promotional offer database 214.

Figure 10A:
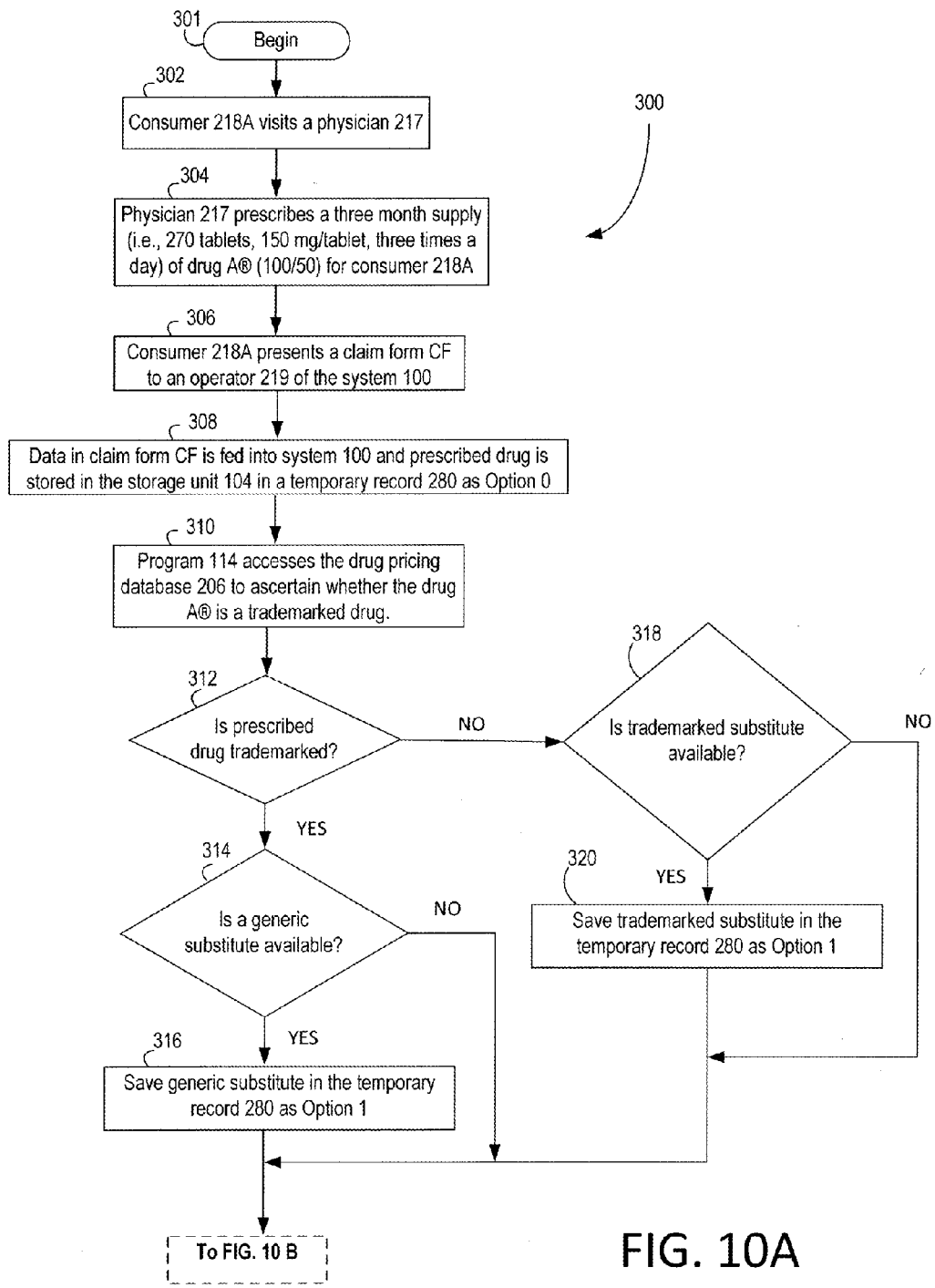
FIGS. 10A through 10B show a flowchart illustrating a method performed in line with the teachings of the present invention.
Figure 10B:
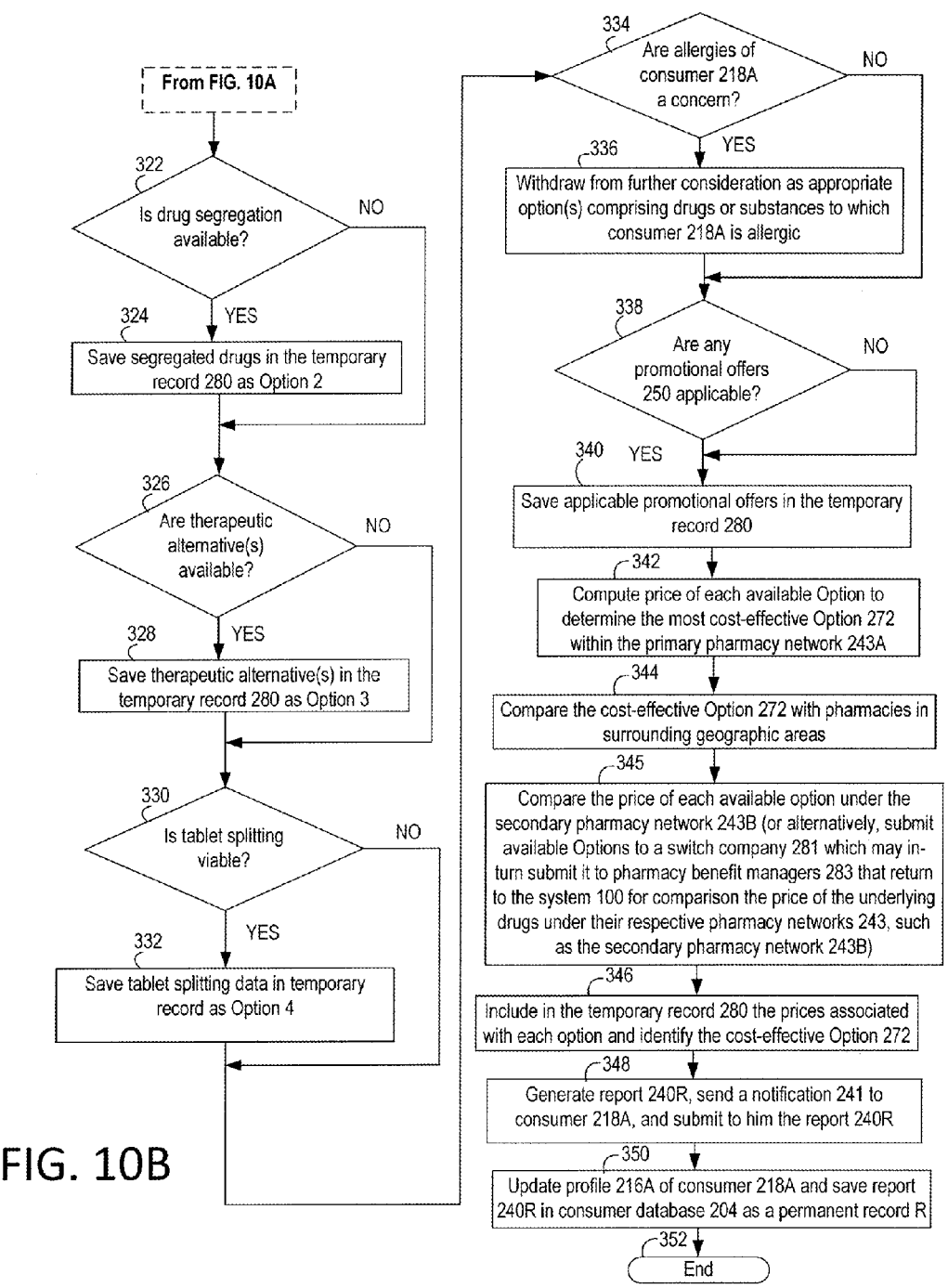

The specifics of the pharmaceutical system 100 and exemplary contents of the individual databases 202 in the pharmaceutical databank 200 are set forth above. The discussion below illustrates how the system 100 may be used to advantageously provide cost-effective alternatives to the consumer 218A using a method 300 (FIGS. 10A-10B). The method 300 may best be illustrated with an example.

The method 300 may begin at step 301, and at step 302, the consumer 218A (i.e., John Doe) may visit a physician 217 (e.g., Dr. Jane A, as shown in the profile 216A of the consumer 218A at field 234). At step 304, the physician 217 may prescribe a three month supply of drug A® (100/50 mg) to the consumer 218A and instruct the consumer 218A to take three 100/50 mg tablets a day. The prescription issued by the physician 217 may then outline, for example, that the consumer 218A is to procure 270 tablets (i.e., 3 tablets/day*3 months*30 days/month=270 tablets) of drug A® (100/50 mg).

At step 306, the consumer 218A may present a claim form CF to an operator (e.g., a pharmacist) 219 of the system 100. Alternatively, an employer or health insurer of the consumer 218A may present to the operator 219 the claim form CF associated with the consumer 218A. In some embodiments, groups of claim forms associated with multiple consumers 218 may be submitted to the operator 219 at one time; for example, an employer may submit to the operator 219 all claim forms associated with each employee that is insured under a health insurance plan carried by the employer.

People of skill in the art will appreciate that the claim form CF associated with the consumer 218A may include, among other things, a request to obtain 270 (100/50 mg) tablets of drug A® (100/50 mg). At step 308, data in the claim form CF may be fed into the system 100 via an automated process (e.g., optical character recognition) and the specifics of the prescribed drug (in this example, Drug A®, 270 tablets, 100/50 mg each) may be stored in the storage unit 104 in a temporary record 280 as Option 0 (see FIG. 11A). In some embodiments, the operator 219 may manually enter the data in the claim form CF into the temporary record 280 (using, for example, the input device 110). While the temporary record 280 in FIG. 11A shows only the specifics of the prescribed drug (i.e., Option 0), people of skill in the art will appreciate that any other data in the claim form CF (e.g., insurance policy information) may similarly be stored in the temporary record 280. In some embodiments, the consumer 218 may be allowed to present the claim form CF to the operator 219 at step 306 remotely (e.g., over the World Wide Web 116).

At step 310, the program 114 may access the drug pricing database 206 to ascertain whether the prescribed drug is trademarked. For example, the program 114 may access cell G5 in the spreadsheet of FIG. 4A illustrating the contents of drug pricing database 206 and conclude that the prescribed drug A® is a trademarked drug. If the program 114 determines at step 312 that the prescribed drug is trademarked, the program 114 may move to step 314 to ascertain whether a generic substitute is available for the prescribed trademarked drug. Specifically, the program 114 may access the generics database 212 (FIG. 7) at step 314 and determine that Drug G (100/50 mg) is the generic version of Drug A® (100/50 mg). At step 316, the program 316 may cause the generic substitute (i.e., drug G in this example) to be added to the temporary record 280 as Option 1 (see FIG. 11B).

If, on the other hand, the program 114 had determined at step 312 that the prescribed drug is not trademarked, the program 114 may have moved to step 318 (instead of step 314) and accessed the generics database 212 to ascertain whether a trademarked substitute is available. For example, if the physician 217 had prescribed drug G to the consumer 218A, the program 114 may have determined that drug A® is the trademarked substitute for drug G, and saved information regarding drug A® in the temporary record 280 as Option 1 at step 320. As mentioned above, while trademarked drugs are generally costlier than their generic counterparts, in some instances, a trademarked drug may end up being cheaper than the generic equivalent (e.g., when a promotional offer 250 is applicable to the trademarked drug).

Once Option 1 is stored in the temporary record 280 at step 316 (or at step 320) as in FIG. 11B, the program 114 may move to step 322 (FIG. 10B) to determine whether drug segregation is available. More specifically, the program 114 may access the drug segregation database 208 to determine if the drug A® is segregable (i.e., if drug A® comprises two or more constituent drugs that may also be purchased separately). The program 114, upon accessing the drug segregation database 208 (FIG. 5) at step 322, may conclude that Drug A® (100/50 mg) is segregable and save the constituent drugs along with their respective strengths (i.e., Drug D (100 mg) plus Drug E (50 mg) in this example) in the temporary record 280 as Option 2 at step 324 (see FIG. 11C). The program 114 may then move to step 326. If the program 114 had determined at step 322 that drug segregation is unavailable, it may have skipped step 324 and moved directly to step 326.

At step 326, the program 114 may ascertain whether one or more therapeutic alternatives are available for the prescribed drug A® (100/50 mg). More specifically, the program 114 may access the therapeutic alternatives database 210 (FIG. 6) at step 326 and determine that a 150/50 mg tablet of drug F is therapeutically equivalent to a 100/50 mg tablet of drug A® (100/50 mg). The program 114 may store this information in the temporary record 280 as Option 3 at step 328 (see FIG. 11D) and then move to step 330. If, on the other hand, the program 114 had determined at step 326 that a therapeutic equivalent is unavailable, the program 114 may have skipped step 328 and moved to step 330 directly.

At step 330, the program 114 may access the drug pricing database 206 (FIG. 4A) determine if tablet splitting is a viable option. Tablet splitting is a form of dose optimization achieved by breaking a higher strength tablet (or pill, capsule, et cetera) into smaller tablets to deliver a prescribed dose. For instance, in this example, the program 114 may determine that 200/100 mg tablets of Drug A® (200/100 mg) are available for purchase (see cell D7, E7 in FIG. 4A) and that each 200/100 mg tablet of Drug A® may be split into two to achieve the prescribed dose of a 100/50 mg tablet of Drug A® (100/50 mg). That is, the program 114 may determine that the consumer 218A could purchase 135 (200/100 mg) tablets of Drug A® (i.e., 270 tablets*(100/50 mg)/tablet=270/2 tablets* ((100*2)(50*2)) mg/tablet=135 tablets*200/100 mg) instead of the 270 (100/50 mg) tablets of Drug A®. The program may at step 332 add this tablet splitting option to the temporary record 280 as Option 4 (see FIG. 11E) and then move on to step 334. Had tablet splitting been unavailable, the program 114 may have moved from step 330 directly to step 334.

At step 334, the program 114 may determine whether the drugs presented in each of the options (i.e., Options 0 through 4 in this example) comprise a drug or other substance to which the consumer 218A is allergic. More specifically, the program 114 may first access the profile 216A (i.e., field 230, FIG. 3) of the consumer 218A in the consumer database 204 and determine that the consumer 218A is allergic to Substance YZ and to Drug C. The program 114 may then access the drug ingredients database 213 and determine that only Drug F (i.e., the therapeutic alternative of Drug A®) in Option 3 of the temporary record 280 is a concern because it comprises the Substance YZ. At step 336, the program 114 may resultantly withdraw Option 3 from further consideration (see FIG. 11F) and move to step 338. Had none of the drugs presented in Options 0 through 4 included Substance YZ or Drug C, the program 114 may have determined at step 334 that allergies of the consumer 218A are not a concern and moved directly to step 338.

At step 338, the program 114 may check whether a promotional offer 250 is applicable to any of the drugs in Options 0, 1, 2, and 4. More specifically, the program 114 may access the promotional offer database 214 (FIG. 9) and determine that a 10% off coupon 250A for drug A® is available and may be applied to Options 0 and 4, but that no promotional offers are applicable to the drugs in Options 1 and 2. The program 114 may add this information regarding the coupon 250A to Options 0 and 4 in the temporary record 280 (see FIG. 11G) at step 340 and then move to step 342. Had no promotional offer 250 been applicable to any of the drugs in Options 0, 1, 2, and 4, the program 114 may have moved from step 338 directly to step 342.

At step 342, the program 114 may compute the prices of each of the options (i.e., Options 0, 1, 2, and 4) in the geographical area of the consumer 218 (i.e., zip code 66214 in this example, see FIG. 3 at field 224) to determine the most cost-effective option 272 under the first pharmacy network 243A (i.e., the network 243 associated with the insurer Green Cross of the consumer 218). More specifically, the program 114 may access the drug pricing database 206 at FIG. 4A and compute that under the first pharmacy network 243A: (a) the lowest price of Option 0, accounting for the coupon 250A, is $369 at Pharmacy ABC (i.e., 270 tablets of Drug A® (100/50 mg)=13 packages*20 tablets/package+1 package*10 tablets/package=>13 packages*$30/package+1 package*$20/package=$410; 10% off $410=$369); (b) the lowest price of Option 1 is $405 at Pharmacy ABC (i.e., 270 tablets of Drug G (100/50 mg each)=27 packages*10 tablets/package=>27 packages*$15/package=$405); (c) the lowest price of Option 2 is $189 (i.e., 270 tablets of Drug D (100 mg each)=27 packages*10 tablets/package=>27 packages*$3/package=$81; 270 tablets of Drug E (50 mg each)=27 packages*10 tablets/package=>27 packages*$4/package=$108; $81 (price of Drug D) plus $108 (price of Drug E)=$189); (d) the lowest price of Option 4 is about $252 at Pharmacy ABC (i.e., 135 tablets of drug A (200/100 mg) 2140 tablets (200/100 mg each)=>7 packages*20 tablets/package=>$40/package*7 packages=$280; 10% off $280=$252). The program 114 may thus determine at step 342 that Option 2 when availed at Pharmacy ABC under the first pharmacy network 243A is the most cost-effective option.

People of skill in the art will appreciate that while in this example the prices of each of the options at Pharmacy ABC were more cost-effective than the prices of these same options at Pharmacy XYZ, that this need not be the case, and that the program 114 may also ultimately compare certain options as availed at Pharmacy ABC with certain other options as availed at Pharmacy XYZ. For example, if a package of 10 tablets of Drug G had been priced at $10 at Pharmacy XYZ instead of $20, the program 114 may have used Pharmacy XYZ's pricing scheme for Option 1 as opposed to Pharmacy ABC's pricing scheme where a package of 10 tablets of Drug G costs $15. Further, people of skill in the art will appreciate that while Option 3 (i.e., the option involving therapeutic equivalents) was withdrawn in this example, that one or more other options may similarly be withdrawn (because of the allergies of the consumer 218A, for example), and that in many instances, there might not be a need to withdraw any option. Moreover, identification of Option 2 (i.e., the drug segregation option) as the cost-effective option 272 is merely exemplary, and those skilled in the art will recognize that another option may similarly be identified as the cost-effective option 272 in differing circumstances. Additionally, while the example illustrated herein is directed to one prescribed drug (i.e., Drug A®), it will be readily apparent that the system 100 may similarly be used to find cost-effective alternatives for multiple drugs within a prescription.

Returning now to the method 300, at step 344, the program 114 may compare the cost-effective Option 272 with the pricing schema of pharmacies under the first pharmacy network 243A in neighboring geographical areas (e.g., zip codes within a twenty mile radius). Specifically, while the program 114 had focused the analysis thus far on pharmacies within the zip code 66214 (cell A1 in FIG. 4A) because the profile 216A of the consumer 218A indicated that he resides in this area (see field 224 in profile 216A at FIG. 3), the program 114 may at step 344 expand the search to neighboring areas and repeat the analysis to ensure that a pharmacy in a neighboring area does not present an option that is more cost-effective than the cost-effective Option 272. Assume for the purposes of this example that Option 2 as availed at Pharmacy ABC in zip code 66214 under the first network 243A subsists as the most cost-effective option 272.

The program 114, heretofore, may have focused its analysis on the first (or primary) pharmacy network 243A because the first pharmacy network 243A is associated with the insurer Green Cross (field 232 in the profile 216A) of the consumer 218A. At step 345, the program 100 may repeat the analysis using the pricing schema of the various pharmacies under other pharmacy networks 243 (i.e., pharmacy networks 243 other than the pharmacy network 243 associated with the primary health insurer Green Cross of the consumer 218A, such as the second (or secondary) pharmacy network 243B (see FIG. 4B)). As discussed above, and as evident from FIGS. 4A and 4B, the same drug (e.g., a package of 10 tablets of drug A® (100/50 mg)) may be obtained at two different prices (e.g., $20 at FIG. 4A under the first pharmacy network 243A; $25 at FIG. 4B under the second pharmacy network 243B) within the same pharmacy (i.e., Pharmacy ABC in zip 66214) depending on the pharmacy network 243 being utilized. These differences in prices may result from one of many reasons. For example, some pharmacy benefit managers may charge the consumers 218 a flat administrative fee per transaction, but otherwise provide the drugs to the consumers 218 at their cost under their respective pharmacy networks 243 (e.g., pharmacy network 243A). Other pharmacy benefit managers, conversely, may charge the consumers 218 under their respective pharmacy networks 243 a percentage of the cost price of the drugs.

The program 114, by comparing the prices of each of the Options 0, 1, 2, and 4 within multiple pharmacy networks 243 (i.e., the first pharmacy network 243A and the second pharmacy network 243B in this example) may effectively pit the different pharmacy networks 243 of the various pharmacy benefit managers against each other. As will be appreciated, this competition may result in additional savings for the consumer 218.

Assume for the purposes of this example that Option 2 as availed at Pharmacy ABC under the first pharmacy network 243A subsists as the cost-effective option 272. However, people of skill in the art will appreciate from the disclosure herein that in many instances, the price of a drug under a secondary pharmacy network (e.g., a discount network, a pharmacy network affiliated with a secondary insurer, et cetera) may end up being more cost-effective than if that drug had been purchased under the primary pharmacy network 243A. Further, while two pharmacy networks 243A and 243B are discussed herein, it will be readily apparent to those skilled in the art that the invention is not so limited, and that many (e.g., ten, twenty, fifty) different pharmacy networks 243 may be seamlessly evaluated to ascertain the most cost-effective option 272 for the consumer 218A.

In some embodiments, at step 345, a switch company 281 may be utilized to transmit the Options 1, 2, and 4 to third parties (e.g., to pharmacy benefit managers 283), who may submit back (e.g., over the World Wide Web) to the system 100 or the operator 219 the prices of the drugs under their respective pharmacy networks 243 for subsequent evaluation by the system 100. In other embodiments, the system 100 may directly submit the Options 1, 2, and 4 to the various pharmacy benefit managers 283 so that the price comparison of these options under the various pharmacy networks 243 could be effectuated. In other embodiments still, as shown in FIGS. 4A-4B, the pricing database 206 may itself include the pricing schema of drugs under different pharmacy networks 243. Irrespective of the mechanism utilized, it will be appreciated that the intent is to: (1) evaluate the prices of drugs in Options 1, 2, and 4 across different pharmacy networks 243 so that the cost-effective Option 272 is revised if it can be fulfilled under a secondary network 243 at an even lower cost; and (2) foster competition amongst the pharmacy benefit managers 283 or other administrators associated with the various pharmacy networks 243 so that the prices of drugs within each pharmacy network 243 are ultimately reduced for the consumer 218A and other consumers 218.

Returning now to the method 300, at step 346, the program 114 may revise the temporary record 280 to include the best price associated with each available option, and identify a cost-effective option (or cost effective alternative) 272 (see FIG. 11H). At step 348, the program 114 may cause the output device 108 (e.g., a printer) to generate the report 240R based on the information in the profile 216A and the temporary record 280.

Figure 12:
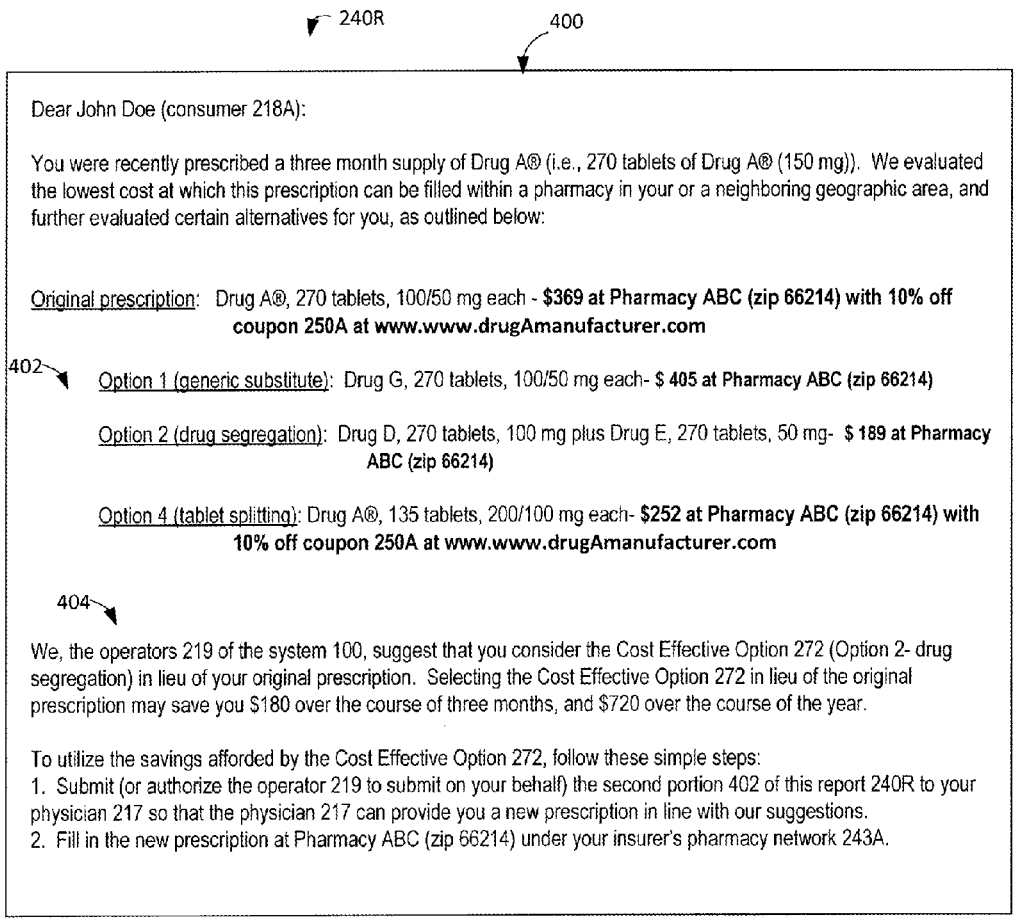
FIG. 12 shows a first portion of a report generated by the system of FIG. 1.
Figure 13:
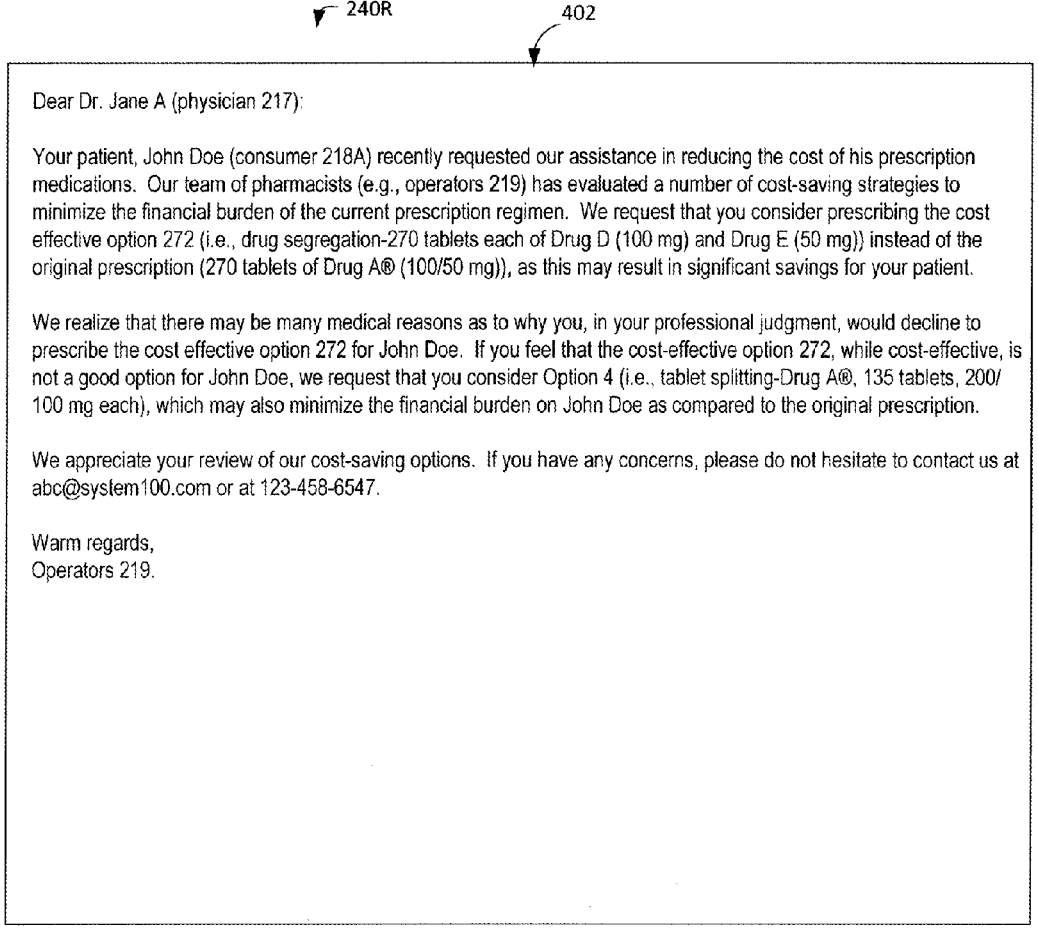
FIG. 13 shows a second portion of the report of FIG. 12.

The report 240R generated by the system 100 may be in one of many formats. For example, as shown in FIGS. 12 and 13, respectively, the report 240R may have a first portion 400 and a second portion 420. The first portion 400 (FIG. 12) of the report 240R may include a first section 402 that outlines details about each option that was analyzed on behalf of the consumer 218A. The first portion 400 of the report 240R may also include a second section 404 that outlines the cost effective option 272 and the savings afforded therefrom, along with instructions on how the consumer 218A may take advantage of the cost effective option 272. In some embodiments, the second section 404 may also provide the consumer 218A with additional information about each of the options that were considered; for example, the second section 404 may set forth information describing therapeutic alternatives, generics, tablet splitting, et cetera. The withdrawn option (Option 3 in this example) may also be listed in the second section 404 in some embodiments, along with the reason(s) due to which this option was withdrawn from consideration. Further, where the cost-effective option 272 is associated with the secondary pharmacy network 243B, the second portion 420 may delineate how the consumer 218A may fulfill the option 272; for example, if the secondary pharmacy network 243B requires the consumer 218A to sign up for a membership or other card before utilizing the secondary pharmacy network 243B, the second portion 420 may list instructions on how this card may be obtained.

The second portion 402 (FIG. 13) of the report 240R may be a note to the physician 217 (i.e., Jane A). More specifically, the second portion (or the note) 402 of the report 240R may request that the physician 217 consider the cost effective option 272 for the consumer 218A in lieu of the original prescription because of the savings associated therewith. The second portion 402 may also outline any other option that is more cost effective than the original prescription (i.e., Option 0) in case the physician 217 disregards the cost effective Option 272 for medical reasons. In some embodiments, the consumer 218A may be asked to submit the second portion 402 (FIG. 13) of the report 240R to the physician 217. In other embodiments, the system 100 may automatically submit the second portion 402 of the report 240R to the physician (e.g., via e-mail, fax, postal mail, et cetera). The physician 217, upon receiving the second portion 402 of the report 240R, may provide the consumer 218A with a new prescription in line with the cost effective option 272 (or another option that is more cost effective than the original prescription), and the consumer 218A may thereafter fill the new prescription at the pharmacy suggested in the report 240R (i.e., pharmacy ABC in this example) to realize the savings.

Returning now to the method 300, once the report 240R is generated at step 348, it may be transmitted to the consumer 218A electronically (e.g., at his e-mail JDoe@abc.com, field 224 in profile 216A at FIG. 3) or via other means (e.g., using postal mail, fax, et cetera). In some embodiments, the report 240R may be saved on a secure website and associated with an account of the consumer 218A on the website, and the consumer may log into his account to access the report 240R. While not required, a notification 241 may be sent to the consumer 218A over a cellular network (e.g., via an SMS message) apprising the consumer 218A of the generation of the report 240R.

At step 350, the program 114 may update the profile 216A of the consumer 218A. For example, the program 114 may update the field 236 in the profile 216A (FIG. 3) to indicate that a prior report 240R has been generated for the consumer 218A. The report 240R may also be saved in the consumer database 204 (or saved in another database and indexed with field 236 of the profile 216A) so that a permanent record R is made of any and all suggestions made to the consumer 218A. The program 114 may then discard the temporary record 280 and end at step 352.

In some embodiments, the consumer 218A may be required to obtain (e.g., purchase at a cost) a discount card 242C before the system 100 is used to evaluate the cost-saving alternatives for him. The discount card 242C may indicate that the consumer 218A has given his authorization to have the system 100 evaluate any of his subsequent prescriptions for cost saving alternatives. The consumer 218A may in some embodiments be required to present the discount card 242C to the pharmacy before taking advantage of the cost-effective Option 272. The discount card 242C may thus further serve as an advertising vehicle for the system 100.

Thus, as has been described, the system 100 may serve as a one-stop-shop for rapidly evaluating many hundreds of possible permutations so that the customer 218A is apprised of the most cost-effective Option 272 available to him. For example, if the customer 218A had been prescribed the drug DIOVAN HCT® (160/12.5 mg), the system 100 may have determined using the generics database 212 and the therapeutic alternatives database 210, respectively, that valsartan/hydrochlorothiazide (160/12.5 mg) is a generic alternative for DIOVAN HCT® (160/12.5 mg) and that losartan/hydrochlorothiazide (100/12.5 mg) is a therapeutic equivalent of DIOVAN HCT® (160/12.5 mg). The system 100 may further have determined using the drug segregation database 208 and the drug pricing database 206, respectively, that DIOVAN HCT® (160/12.5 mg) may be segregated into DIOVAN® 160 mg and hydrochlorothiazide 12.5 mg and that a tablet of DIOVAN HCT® 320 mg/25 mg could be split into two (i.e., tablet splitting) to achieve the prescribed drug. The system 100 may then have, in line with the disclosure herein, evaluated each of these options to determine and convey to the consumer 218A the option that proved to be most cost-effective.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described.

The invention claimed is:

1. A computer implemented method for determining a cost effective option for a first drug of a first strength prescribed to a patient by a physician, the cost effective option being one of an original option, a generics option, a therapeutic alternatives option, a drug segregation option, and a tablet splitting option, the method comprising steps:

a) using a pharmaceutical database to identify a second drug that is a generic alternative of the first drug;

b) using the pharmaceutical database to identify a third drug that is a therapeutic alternative of the first drug;

c) using the pharmaceutical database to identify both a fourth drug and a fifth drug into which the first drug can be segregated;

d) using the pharmaceutical database to identify a sixth drug that comprises the first drug at a second strength, the second strength being greater than the first strength;

e) storing in a non-transitory computer memory a preliminary option set consisting of the first drug as the original option, the second drug as the generics option, the third drug as the therapeutic alternatives option, the fourth and the fifth drugs collectively as the drug segregation option, and the sixth drug as the tablet splitting option;

f) using a profile of the patient to identify a drug and a substance to which the patient is allergic;

g) using the pharmaceutical database to identify ingredients of each of the first, the second, the third, the fourth, the fifth, and the sixth drug; and deleting from the non-transitory memory any said option associated with the drug or the substance to which the patient is allergic, whereby forming from the preliminary option set a final option set stored in the non-transitory memory;

h) subsequent to step (g), using the pharmaceutical database to identify a promotional offer applicable to any said option in the final option set;

i) using the pharmaceutical database to determine a respective price of each said option in the final option set;

j) automatically identifying one of said options in the final option set as the cost effective option, the price of the cost effective option being lower than the respective prices of all other options in the final option set;

k) generating a report for the patient using an output device, the report having a first portion for the patient and a second portion for the physician, each of the first and second portions listing the cost effective option; and l) automatically submitting the second portion to the physician;

wherein each of the steps (a)-(l) is performed at least in part by a computer processor.

2. The method of claim 1 wherein the price of the cost effective option is the lower of a first network price and a second network price, the first network price being associated with a first pharmacy network and the second network price being associated with a second pharmacy network.

3. The method of claim 2 wherein the first pharmacy network is associated with a primary health insurer of the patient.

4. The method of claim 2 wherein the first pharmacy network is a discount network.

5. The method of claim 1 wherein the price of the cost effective option is the lower of a first pharmacy price and a second pharmacy price, the first pharmacy price being associated with a first pharmacy and the second pharmacy price being associated with a second pharmacy.

6. The method of claim 5 wherein each of the first pharmacy and the second pharmacy is selected to be within a geographical area of the patient.

7. The method of claim 1 further comprising the step of sending a notification to the patient upon the generation of the report; and wherein at least one of the first portion and the second portion includes a listing of every option in the final option set.

8. The method of claim 1 further comprising the step of updating the profile after the generation of the report.

9. The method of claim 1 further comprising the step of using optical character recognition to identify data on a claim form associated with the patient.

10. The method of claim 1 wherein the price of the cost effective option is determined after considering the respective prices of each of said options in the final option set in at least two pharmacies and under at least two networks.

\* \* \* \* \*